US 6,621,013 B2

(12) United States Patent
Tanida et al.

(10) Patent No.: US 6,621,013 B2
(45) Date of Patent: Sep. 16, 2003

(54) LIVING BODY MEASURING DEVICE HAVING FUNCTION FOR DETERMINING MEASURED SUBJECT

(75) Inventors: Daisuke Tanida, Tokyo (JP); Fumiko Nakagawa, Tokyo (JP); Masayuki Kenmochi, Senboku-Machi (JP); Yuki Sato, Omagari (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 10/155,991

(22) Filed: May 29, 2002

(65) Prior Publication Data

US 2002/0179338 A1 Dec. 5, 2002

(30) Foreign Application Priority Data

May 29, 2001 (JP) ........................ 2001-160534

(51) Int. Cl.[7] .......................... G01G 19/32; A61B 5/05; A61B 5/00
(52) U.S. Cl. ............................ 177/4; 177/5; 177/25.19; 177/245; 600/547; 340/5.82
(58) Field of Search .................... 177/25.16, 25.19, 177/25.13, 245, 4, 5; 600/547, 554, 372, 382, 384; 340/5.82

(56) References Cited

U.S. PATENT DOCUMENTS

| 4,366,873 A | * | 1/1983 | Levy et al. ............... 177/25.19 |
| 4,423,792 A | * | 1/1984 | Cowan ..................... 177/25.19 |
| 4,773,492 A | * | 9/1988 | Ruzumna .................. 177/25.19 |
| 4,831,242 A | * | 5/1989 | Englehardt et al. ...... 177/25.19 |
| 4,844,187 A | * | 7/1989 | Jabero ..................... 177/25.19 |
| 5,579,782 A | * | 12/1996 | Masuo ....................... 600/547 |
| 5,719,950 A | * | 2/1998 | Osten et al. ............... 340/5.82 |
| 5,720,296 A | * | 2/1998 | Cha ........................... 600/372 |
| 5,729,905 A | | 3/1998 | Mathiasmeier et al. ....... 33/3 R |
| 6,038,465 A | * | 3/2000 | Melton, Jr. .............. 177/25.19 |
| 6,256,532 B1 | * | 7/2001 | Cha ........................... 600/547 |
| 6,280,396 B1 | * | 8/2001 | Clark ......................... 600/547 |
| 6,321,112 B1 | * | 11/2001 | Masuo ....................... 600/547 |

FOREIGN PATENT DOCUMENTS

| DE | 198 30 058 | 3/2000 |
| JP | 6-142065 | 5/1994 |
| JP | 11-076177 | 3/1999 |
| JP | 2001-204705 | 7/2001 |
| JP | 2001-204706 | 7/2001 |
| WO | WO99/52425 | 10/1999 |

* cited by examiner

Primary Examiner—Randy Gibson
(74) Attorney, Agent, or Firm—McDermott, Wll & Emery

(57) ABSTRACT

An object of the present invention is to provide a living body measuring device which, once the personal information having been set therein, executes an arithmetic operation simply by making a measurement without requiring a user to remember his/her personal memory number.

The living body measuring device of the present invention stores the measured body weight value and/or bioelectrical impedance value as well as the personal body information set in the initial stage, compares the measured values with those stored values, and determines a current subject who is being measured by considering the most proximal values to be the data associated with the measured subject, thereby calculating a body-related index automatically. Especially, if both of the bioelectrical impedance and the body weight are used, then the determination may be more accurate.

11 Claims, 9 Drawing Sheets

FIG. 6
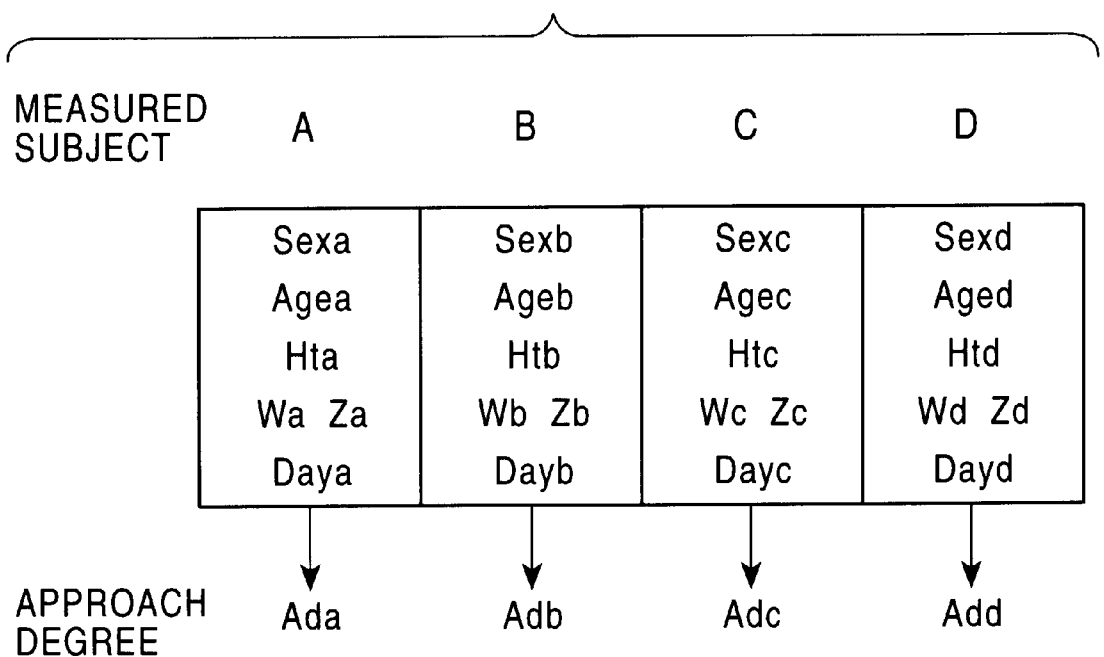
IN THE CASE OF Adc < Ada < Adb < Add
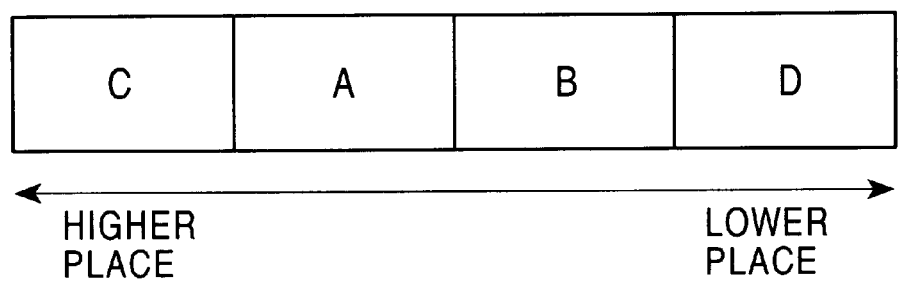

FIG. 7A

⓷  FEMALE 20 YEARS 165.5 cm 48.6 kg
22.5 %

FIG. 7B

⓶  FEMALE 45 YEARS 160.0 cm 48.6 kg
25.7 %

# LIVING BODY MEASURING DEVICE HAVING FUNCTION FOR DETERMINING MEASURED SUBJECT

FIELD OF THE INVENTION

The present invention relates to a device for measuring a body weight and/or a bioelectrical impedance for a plurality of subjects and calculating an index relating to a body based on those measured values, and in particular, relates to a technology for automatically identifying a subject who is being measured.

DESCRIPTION OF THE PRIOR ART

There has been such a prior art body fat measuring device as shown in FIG. 9, which allows for a condition to be used among a plurality of users. This prior art device comprises a memory for storing personal data (i.e. sex, age and body height) for a plurality of users, and calculates and indicates a percent body fat and a body fat mass of a measured subject based on the personal data having been stored in this memory, a body weight value obtained by body weight measuring means and a bioelectrical impedance value obtained by bioelectrical impedance measuring means.

Although in such a prior art body fat measuring device described above, once the personal information has been stored therein, the setting procedures would not be required again, yet upon measurement, a user has been requested to enter his/her personal memory number or to press one of the measuring switches 50 corresponding to respective memory numbers. To satisfy this requirement, the user has to remember the memory number which has been established in the device, and if the user forget the memory number, he/she is required to read out the stored information by sequentially pressing the measuring switches corresponding to every memory number so as to confirm the stored information, or otherwise he/she is required to repeat the setting procedure again.

Further, in the case where the body fat measuring device includes the measuring switch 50 provided for each individual as shown in FIG. 9, the number of components has been increased, resulting in a cost increase. Alternatively, such a device that uses numeric keys and/or a cross key to enter the personal memory number does not need any measuring switch to be provided, but an input operation of the number is bothering and in this case again, the user has to remember his/her memory number. Accordingly, such a user having a poor memory like an elder person may find it difficult to handle that type of device.

SUMMARY OF THE INVENTION

The present invention has been made in the light of the problems discussed above, and an object thereof is to provide a living body measuring device which, once the personal information having been set therein, executes an arithmetic operation simply by making a measurement without requiring a user to remember his/her personal memory number.

According to an aspect of the present invention, a living body measuring device having a function for determining a measured subject, comprises an input unit, a bioelectrical impedance measuring unit, a storage unit and an arithmetic unit,
wherein
said input unit enters information relating to a body of a subject;
said bioelectrical impedance measuring unit measures a bioelectrical impedance of said subject;
said storage unit stores data for a plurality of subjects, said data representing the body-related information entered from said input unit and the measured bioelectrical impedance values; and
said arithmetic unit determines who is the measured subject by comparing the measured current bioelectrical for the plurality of subjects stored in said storage unit, and calculates an index relating to the body of the determined subject based on the body information of the determined subject stored in said storage unit and the measured current bioelectrical impedance value.

According to another aspect of the present invention, a living body measuring device having a function for determining a measured subject, comprises an input unit, a body weight measuring unit, a bioelectrical impedance measuring unit, a storage unit and an arithmetic unit,
wherein
said input unit enters information relating to a body of a subject;
said body weight measuring unit measures a body weight of said subject;
said bioelectrical impedance measuring unit measures a bioelectrical impedance of said subject;
said storage unit stores data for a plurality of subjects, said data representing the body-related information entered from said input unit and measured body weight values and bioelectrical impedance values; and
said arithmetic unit determines who is the measured subject by comparing the measured current body weight value and bioelectrical impedance value with the body weight values and bioelectrical impedance values for the plurality of subjects stored in said storage unit, and calculates an index relating to the body of the determined subject based on th body information of the determined subject stored in said storage unit and the measured current body weight value and bioelectrical impedance value.

According to an embodiment of the present invention, a living body measuring device having a function for determining a measured subject further comprises a clock unit,
wherein
said clock unit clocks a current day and time;
said storage unit also stores a measurement day and time; and
said arithmetic unit also uses an elapsed day count from a last measurement day stored in said storage unit to a current measurement day in order to make a determination of the subject.

According to another embodiment of the present invention, a living body measuring device having a function for determining a measured subject is characterized in that:
said storage unit stores measured values for each subject on the basis of a measurement time slot, and said arithmetic unit makes a determination of a subject by comparing the stored measured values in the same time slot as the current time with the current measured value.

According to still another embodiment of the present invention, a living body measuring device having a function for determining a measured subject further comprises a switch
wherein
said switch is activated to measure a body weight and a bioelectrical impedance upon a subject putting his/her body on said device.

According to still another embodiment of the present invention, a living body measuring device having a function for determining a measured subject, said device further comprises a display unit,
wherein
said display unit indicates an index relating to a body of a subject, said index representing a result from the calculation by said arithmetic unit, and
said display unit also indicates the body information stored in said storage unit and used in the calculation as well as the result indication.

According to still another embodiment of the present invention, a living body measuring device having a function for determining a measured subject is characterized in that:
said arithmetic unit recalculates the index relating to the body based on a selected information if the information to be used in the calculation is changed during the indication of the index relating to the body.

According to still another embodiment of the present invention, a living body measuring device having a function for determining a measured subject is characterized in that:
a bioelectrical impedance value and a body weight value for a subject stored in said storage unit are updated at each time when the measurements are made.

According to still another embodiment of the present invention, a living body measuring device having a function for determining a measured subject is characterized in that:
said arithmetic unit makes a determination of a subject in favor of a result obtained from a comparison of the body weights between the comparison of body weight values and the comparison of bioelectrical impedance values.

According to still another embodiment of the present invention, a living body measuring device having a function for determining a measured subject, said device further comprises an electrode,
wherein
said electrode measures a sole length of a subject,
said electrode comprising a plurality of sub-electrodes;
said storage unit stores a measured sole length as well as the other information; and
said arithmetic unit determines who is a measured subject by further using a result from a comparison of the measured sole length with the sole lengths stored in said storage unit for a plurality of subjects.

BRIEF DESCRIPTION OF THE DRAWINGS

FIG. 6 is a schematic diagram of a memory region in a storage unit of the body fat meter according to the embodiment of the present invention;

FIGS. 7A and 7B show examples of displays of results of the body fat meter according to the embodiment of the present invention;

DESCRIPTION OF THE MODE FOR CARRYING OUT THE PRESENT INVENTION

A living body measuring device of the present invention compares a measured bioelectrical impedance value and/or body weight value with those values for a plurality of users stored in a storage unit, determines the most proximal values to be data for a user being measured, and reads out the data associated with that determined user to use in an arithmetic operation.

To explain this with reference to the actual case, for example, where one device is used in a family, generally a father, a mother and a child have distinguishably different body types and thus have different body weights and bioelectrical impedances, respectively. These body weight values and bioelectrical impedance values can be changed by the growth of body in association with aging and/or by an intentional weight reduction activity, but no significant changes would be observed in those values in such a short term as one day or one week period.

On the basis of those body features as described above, the living body measuring device of the present invention stores, upon initial setting of personal body information, a measured body weight value and/or bioelectrical impedance value at that time, and identifies a current subject being measured by comparing the measured values with the stored those values so as to calculate a body-related index automatically. Especially, if both of the bioelectrical impedance and the body weight are used, then the determination may be more accurate.

DESCRIPTION OF THE PREFERRED EMBODIMENTS

Figure 1:
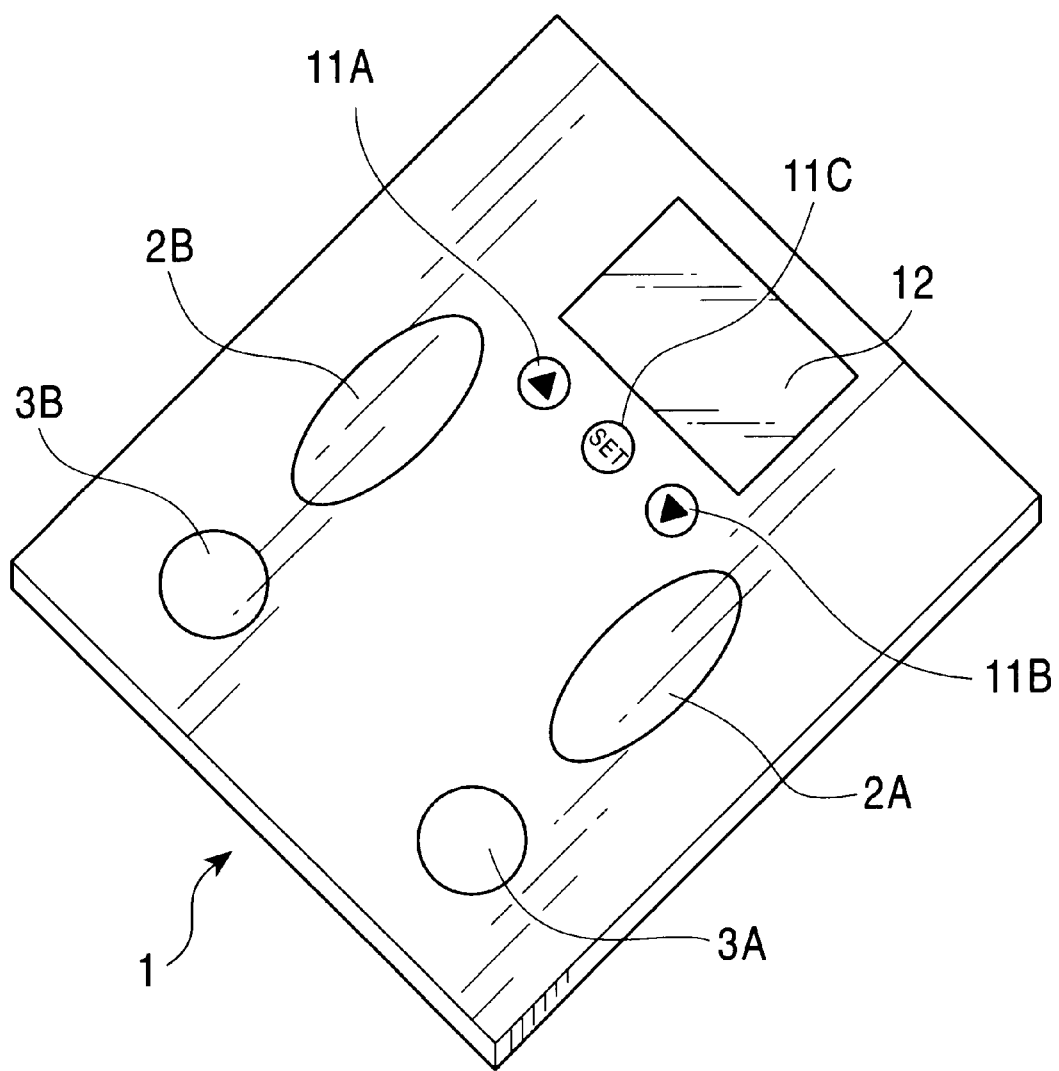
FIG. 1 is a perspective external view of a body fat meter according to an embodiment of the present invention.
Figure 2:
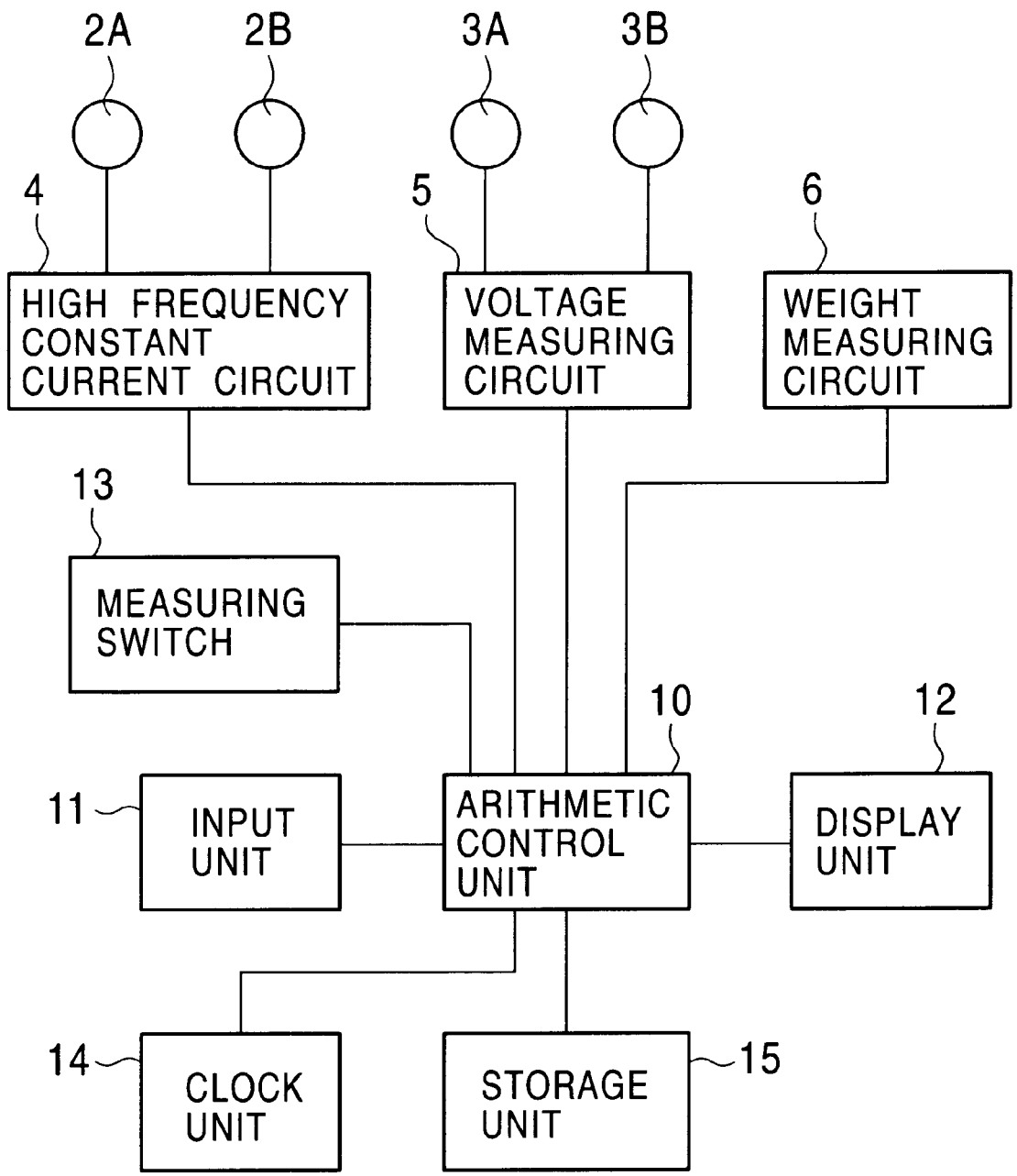
FIG. 2 is a block diagram of the body fat meter according to the embodiment of the present invention.

An embodiment of a living body measuring device of the present invention will now be described with reference to the attached drawings. FIG. 1 is a perspective external view of a body fat meter 1 capable of measuring a body weight and a percent body fat, according to an embodiment of the present invention. FIG. 2 is a block diagram showing an internal connecting condition in the body fat meter 1 shown in FIG. 1.

A total of four electrodes, a pair of current supplying electrodes 2A and 2B and a pair of voltage measuring electrodes 3A and 3B, are disposed on an upper face of the body fat meter 1 as impedance measuring means so that an impedance between feet of a user can be measured.

The pair of current supplying electrodes 2A and 2B is coupled to a high frequency constant current circuit 4 for applying a weak high frequency constant current. The other pair of voltage measuring electrodes 3A and 3B is coupled to a voltage measuring circuit 5 for measuring an amount of voltage drop in said constant current. Further, the body fat meter main body 1 includes in an inside thereof a weight measuring circuit 6 as body weight measuring means for measuring a body weight representing a weight of a user when the user puts his/her body on the body fat meter 1. The voltage measuring circuit 5 and the weight measuring circuit 6 are connected to an arithmetic control unit 10 serving as arithmetic means for executing a conversion from an analog value to a digital value, a calculation of a percent body fat, and a variety of control operations.

Further, an input unit 11 serving as input means comprises a total of three switches, an up switch 11A, a down switch 11B and a setting switch 11C.

The body fat meter 1 further comprises a display unit 12 serving as display means for indicating an entered personal body information and a measured body weight as well as a calculated percent body fat.

Further, a measuring switch 13 is arranged on an under face of the body fat meter 1, in which said measuring switch 13 is normally out of contact with a floor and accordingly in OFF state, and when a subject put himself/herself on the upper face of the body fat meter 1 for a measurement, it comes into contact with the floor, a load exceeding a prescribed level is applied thereto and thereby it turns to ON state.

The body fat meter 1 contains in the inside thereof a clock unit 14 serving as clock means for clocking a current day and time, and a storage unit 15 serving as storage means for storing the personal information and/or the measured body weight values and bioelectrical impedance values for a plurality of users.

An operation of the body fat meter, which is an embodiment of the living body measuring device according to the present invention, will now be described, and it is to be noted that since the measurement and calculation of the percent body fat is disclosed in the gazette of Japanese Patent Publication No. Hei 5-49050 or the like and products of such type have been available in the market, therefore only a brief explanation will be herein described.

Figure 3:
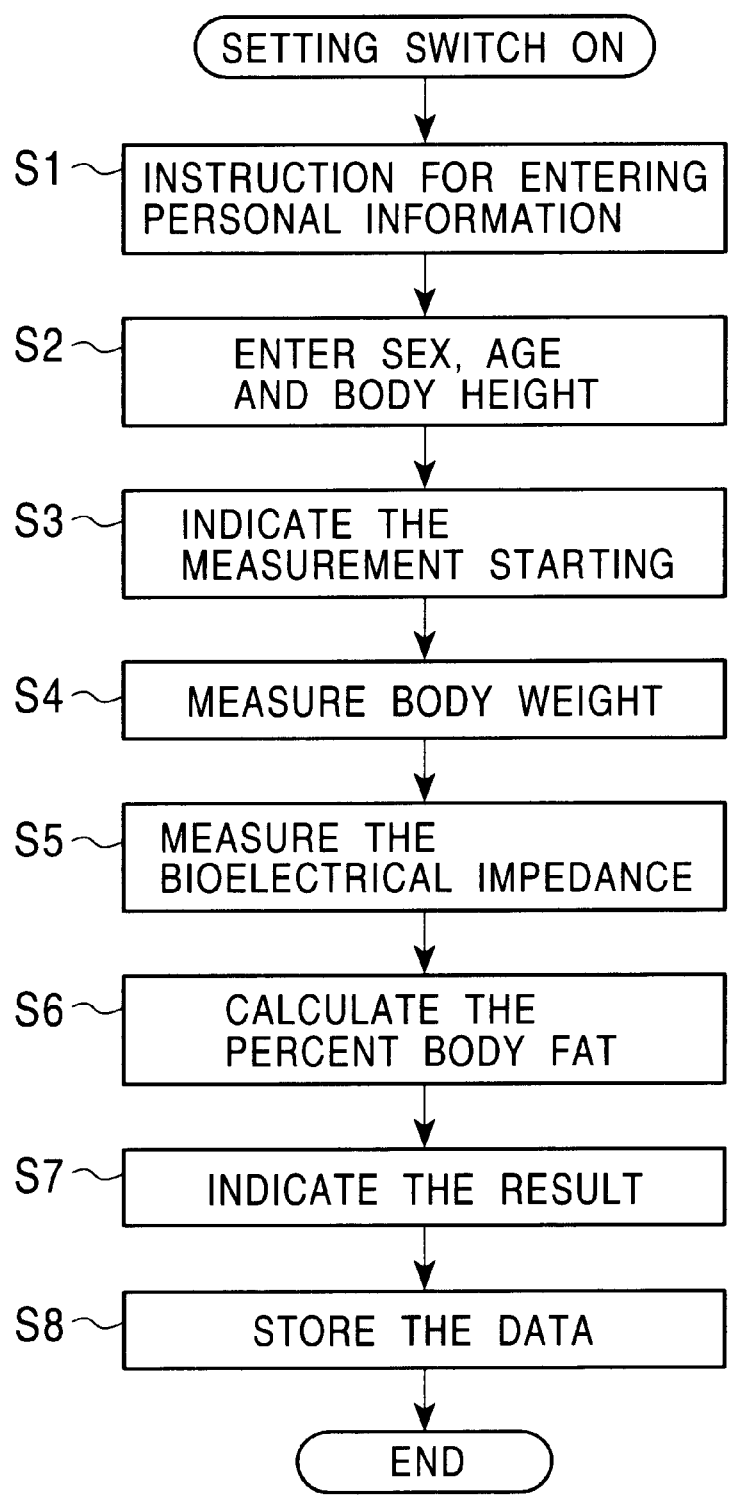
FIG. 3 is a flow chart in a setting mode of the body fat meter according to the embodiment of the present invention.

FIG. 3 is a flow chart showing a flow of operation in a setting mode of the body fat meter 1.

In this body fat meter 1, it is required to establish therein a personal body information of a user in advance if it is a first measurement for that user.

When the setting switch 11C is pressed, the body fat meter 1 is turned into the setting mode, and the display unit 12 shows an indication for prompting the user to enter his/her personal information (step S1).

Then, the user uses the up switch 11A and/or the down switch 11B to modify the information indicated in the display unit 12 so as to enter his/her sex, age and body height (step S2).

When the setting procedure of the personal information has been completed, an indication for prompting the user to step on the upper face of the body fat meter 1 is displayed (step 3), and then the user puts his/her body on the body fat meter 1 with his/her toe and heel of right foot touching with the current supplying electrode 2A and the voltage measuring electrode 3A, respectively, and with his/her toe and heel of left foot touching with the current supplying electrode 2B and the voltage measuring electrode 3B, respectively. At this timing, the weight measuring circuit 6 measures the body weight of the user (step S4).

Subsequently, a bioelectrical impedance is measured. An alternating current supplied from the high frequency constant current circuit 4 is applied into the body of the measured subject via the current supplying electrodes 2A and 2B, and a voltage between the voltage measuring electrodes 3A and 3B is measured by the voltage measuring circuit 5, and then the arithmetic control unit 10 calculates the bioelectrical impedance value of the measured subject (step S5).

The percent body fat of the measured subject is calculated based on the measured body weight value and bioelectrical impedance value and the entered body height. An arithmetic formula used in this percent body fat calculation is different in dependence on the entered sex and age, and therefore the arithmetic control unit 10 is adapted to select a suitable arithmetic formula to make the calculation (step S6).

The calculated percent body fat and the measured body weight are indicated in the display unit 12 (step S7).

The arithmetic control unit 10 stores the entered data representing the sex, the age and the body height, and the currently measured body weight value and bioelectrical impedance value as a set of data associated with one measured subject in an personal data memory area within the storage unit 15 (step S8). The setting mode is now completed, and the power supply of the body fat meter is automatically turned off.

Then a measuring mode will be described.

Figure 4:
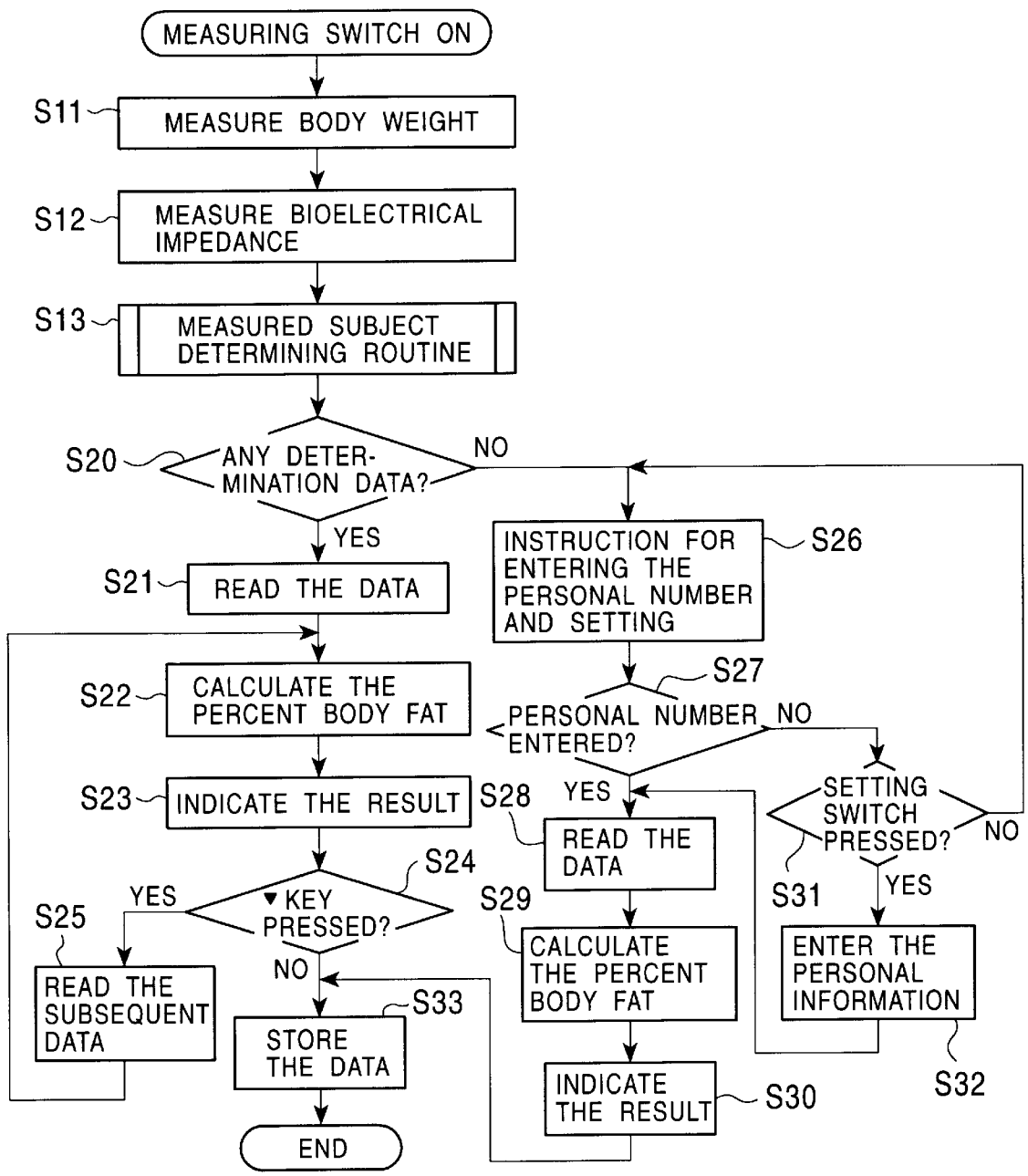
FIG. 4 is a flow chart in a measuring mode of the body fat meter according to the embodiment of the present invention.

FIG. 4 is a flow chart showing a flow of operation of the measuring mode.

When the subject puts himself/herself on the body fat meter 1 in its OFF state for measurement, the measuring switch 13 disposed on the under face of the body fat meter 1 is turned on and the operation is switched into the measuring mode.

Then, the body weight and the bioelectrical impedance of the user are measured, and these processes are carried out similarly to those steps S3 and S4 as shown in the preceding setting mode (step S11, S12).

Figure 5:
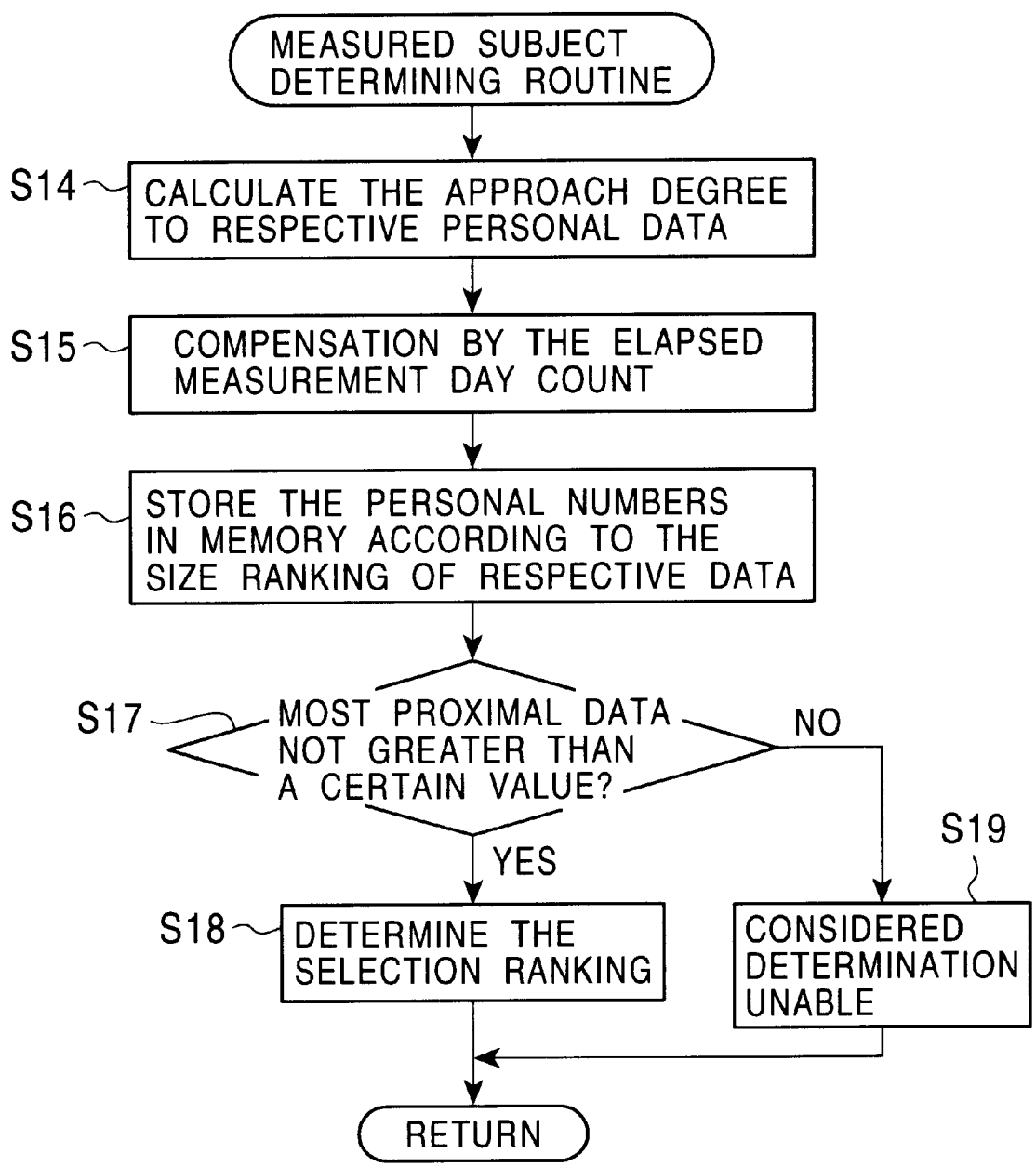
FIG. 5 is a flow chart of a measured subject determining routine of the body fat meter according to the embodiment of the present invention.

Once the body weight and the bioelectrical impedance values have been measured, the user is identified by a user determining routine at step S13. A flow of this user determining routine is shown in FIG. 5.

How to determine the user will now be described with reference to FIG. 6.

FIG. 6 shows a schematic diagram of a memory region of the storage unit. The storage unit 15 contains the personal body information representing the sex "Sex", the age "Age" and the body height "Ht" for four users, A, B, C and D, respectively, which have been set in the setting mode, as well as the body weight value "w" and the bioelectrical impedance value "Z" to be used as reference values for those users, respectively, which have been also stored therein.

In operation, the process performs arithmetic of an approach degree for comparing the current measured value with the registered value for each individual.

In this embodiment, the process calculates the approach degree "Ad", assuming that the registered body weight value is "Wm", the registered bioelectrical impedance value "Zm", the currently measured body weight value "W", and the bioelectrical impedance value "Z".

$$Ad = |W - Wm| \times \alpha + |Z - Zm| \times \beta$$

where, $\alpha$ and $\beta$ are weighting factors, which compensate for the weight contribution of the body weight value and the bioelectrical impedance value to the approach degree.

Generally, a change called as a circadian rhythm occurs in the body weight value and the bioelectrical impedance value. The bioelectrical impedance measured between one foot and the other foot is higher at night through to the morning during the user sleeping, which may be getting lower gradually after the user having got up as he/she becomes active. On the other hand, the body weight value may also have a change within a day caused by such behaviors as eating, drinking and defecation, but this variation may be appeared relatively stable as compared with the variation in bioelectrical impedance.

Accordingly, it is considered that the variation in the body weight is smaller than that in the bioelectrical impedance in a short period on condition that the user does not make any particular exercises or weight reduction activities during that short period, and therefore it is believed that the measurements, if made regularly in the same time slots, indicate constant values, and consequently it is also believed that preferably the setting of α>β should be employed so as for the change in body weight to contribute more to the approach degree.

This calculation of approach degree is made for all of the registered reference values for respective individuals, and in the determination, the user having a smaller approach degree value is ranked in a higher place.

Accordingly, in the measured subject determining routine, the reference body weight and bioelectrical impedance values for respective individuals and the corresponding values measured actually are used to calculate the approach degree (step S14).

Further, based on the number of elapsed days counted from the last measurement day, the calculated approach degree is compensated for.

In this embodiment, it is assumed that the larger the elapsed day count is, the larger value is added to the approach degree. For example, if 10 days has elapsed from the last measurement day, the compensation may be+10X, or if 30 days, it may be+30X (where, the X is a coefficient). The approach degree is compensated for by way of this calculation (step S15). In case of the approach degrees being more or less same according to this compensation, newly stored data is placed in favor with respect to formerly stored data. Accordingly, the elapsed day count is determined from the measure data "Day" stored in the memory and the measured day representing the current day so as to make the compensation.

The personal numbers are stored in the memory in ascending order according to this calculated approach degree (step S16).

Then, it is determined whether the approach degree for the personal number ranked in the top place in determination is not exceeding a certain value (step S17).

If not exceeding the certain value, it is determined that the determination is satisfied, the current approach degree is determined as the selection ranking (step S18), and the measured subject determining routine comes to an end.

On contrast, if the approach degree of the personal number ranked in the top place in determination is exceeding the certain value, then it is considered that the accuracy of determination is low and thus the determination on the measured subject is unable (step S19), and the measured subject determining routine comes to an end.

At the step S20 of FIG. 4, the determination result in the measured subject determining routine is confirmed. In this step, if the determination of the measured subject has been carried out normally, the body information data for the measured subject ranked in the topmost place in the determination result is read out from the storage unit 15 (step S21).

The arithmetic control unit 10 calculates the percent body fat based on the measured body weight value and bioelectrical impedance value, and the read-in personal information (step S22).

Thereafter, the result is indicated as shown in FIG. 7A. As shown in FIG. 7A, in addition to the measured body weight value and the percent body fat are indicated the sex, the age and the body height, which are the data used in the measurement. The circled number is representing the personal number.

Then, it is determined whether the down switch 11B has been pressed or not (step S24). This is for enabling the measured subject to confirm whether or not the determined result is wrong, and if the down switch 11B has been pressed, the body information data for another measured subject who has been ranked in the second highest place in the determination is read in, and the process returns to the step S22 to use that data to recalculate the percent body fat (step S25). In that case, the body information data associated with the runner-up candidate in the determination is indicated as shown in FIG. 7B, and also the percent body fat calculated based on that data is indicated. As discussed above, the process is designed such that the data associated with the runner-up candidates are sequentially read in by pressing the down switch 11B so as to recalculate the percent body fat.

If the determination of the measured subject has been failed at step S20, the instruction is indicated in the display unit 12, prompting the user to input the personal memory number directly or to make a new setting (step S26)

Then, it is determined whether or not the personal memory number has been entered by using the up switch 11A or the down switch 11B (step S27), and if the personal memory number has been entered, the body information data associated with the entered personal memory number is read out from the storage unit 15 (step S28), and the arithmetic control unit 10 executes the calculation of the percent body fat based on the read-in body information data (step S29), and indicates the result in the display unit 12 (step S30).

If the personal number has not been entered at step S27, then it is determined whether the body information is going to be newly entered or not by judging that the setting switch 11C is pressed or not (step S31).

If the setting switch 11C is pressed in this step, the instruction is indicated prompting the user to enter the sex, the age and the body height as the personal information in the similar manner to those steps S1 and S2 in the preceding setting mode, and the measured subject uses the up switch 11A and/or the down switch 11B to make a setting (step S32). Thereafter, the process moves to the step S29 to calculate the percent body fat, and the result is also indicated.

If the down switch 11B is not pressed at step S24 or after the result has been indicated at the step 30, the reference value data is updated. That is, currently measured body weight value and bioelectrical impedance value are stored as new reference values in the personal data of the measured subject (step S33).

Through the above procedures, all the measurement processes are now completed and the power supply of the body fat meter 1 is turned off.

In the above description, one embodiment of the present invention has been illustrated, but the method for determining the measured subject is not limited to the method as illustrated in this embodiment. For example, in an alternative method, threshold values are set for the stored body weight value and bioelectrical impedance value, respectively, and the determination may be made based on whether or not the measured values are within the ranges defined between the threshold values.

Further, although in the above description, the device for measuring the bioelectrical impedance between one foot and the other foot as well as the body weight has been described, the present invention is not limited to this type of device but the device may make a comparison exclusively between the bioelectrical impedance values to determine the measured subject without measuring the body weight. Further, as to the site of measurement for the bioelectrical impedance, the measurement may be conducted between one hand and the other hand or between one hand and one foot. Alternatively, a plurality of electrodes may be used to measure the bioelectrical impedance at a plurality of sites of the user, which increases the number of parameters available for the comparison, and thereby makes it possible to identify the user more reliably.

Further, although in the above description, the body weight and the bioelectrical impedance have been employed as the parameters used for identifying the user, various other body parameters of the user may be used for the identification.

Figure 8:
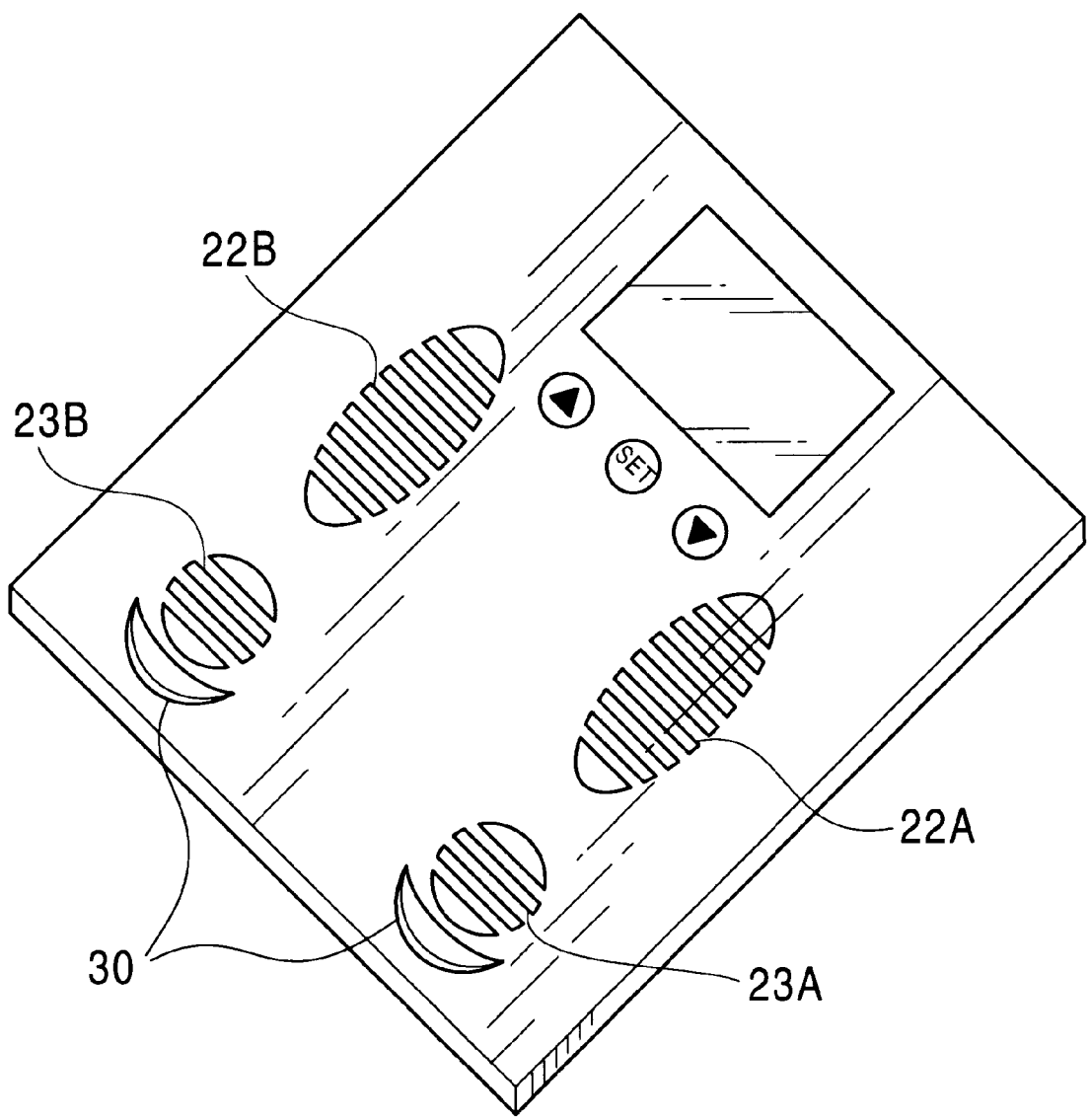
FIG. 8 is a perspective external view of a body fat meter according to another embodiment of the present invention.

For example, such a body fat meter as shown in FIG. 8 may be conceivable. In this body fat meter, a pair of left and right current supplying electrodes 22A and 22B and a pair of voltage measuring electrodes 23A and 23B comprise respectively groups of multi-divided electrodes arranged in parallel with each other, in which the connections between the respective electrodes may be switched internally in the body fat meter. In addition, a heel guide 30 is arranged in a side of the voltage measuring electrode opposite to the current supplying electrode, thereby ensuring that the heel portion of the measured subject comes in touch with the voltage measuring electrode. In this body fat meter, since the plurality of electrodes are provided, it becomes possible to identify the electrode which the sole of the user is in touch with and thereby the sole length (foot size) of the measured subject can be measured. If the sole length herein measured is used, in addition to the measurements of the body weight value and the bioelectrical impedance value, to determine the user, it becomes possible to make a more accurate determination of the measured subject.

Alternatively, if a body fat meter comprises a body height meter capable of measuring the body height, then the body height may also be used as a parameter for the determination of the user.

Figure 9:
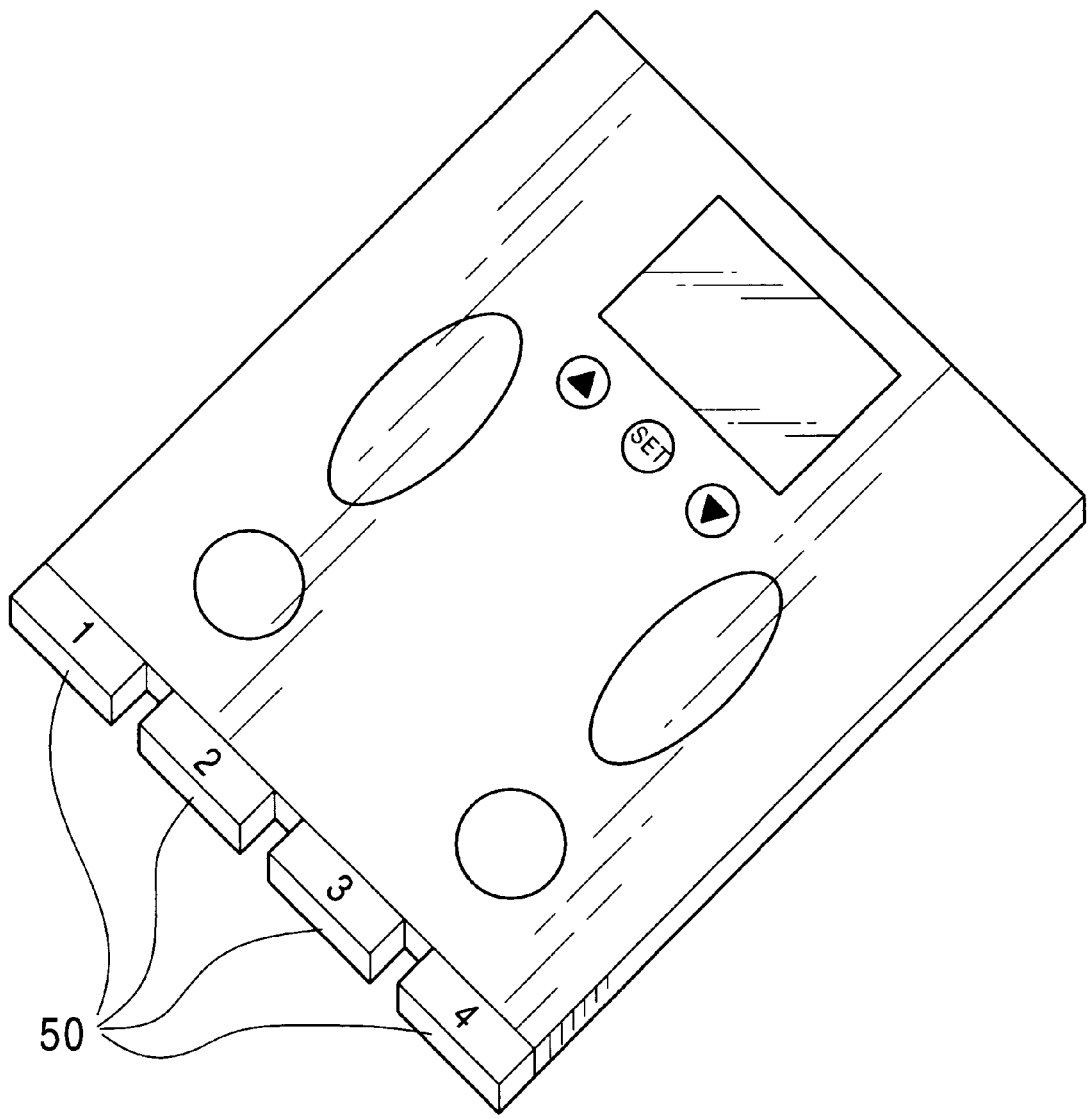
FIG. 9 is a perspective external view of a body fat meter according to the prior art.

Further, although the embodiments of the body fat meter as illustrated herein includes no personal measurement starting switches, the body fat meter according to the present invention may comprise the personal measurement starting switch similarly to the prior art body fat meter as shown in FIG. 9. In that case, the body fat meter may be designed such that if the result of the personal determination has been an erroneous determination, the personal measurement starting switch may be required to be pressed and the data corresponding to the pressed switch is called out for recalculation.

Further, although in the above discussion, the explanation has been directed to the device which performs the calculation of the percent body fat representing a ratio of the body fat with respect to a body constitution of a measured subject as an index relating to the body for which the arithmetic operation is executed, the present invention may be applied also to such a device that calculates a body fat mass representing an amount of the body fat or a visceral fat ratio or mass representing the fat put on the surrounding of the intra-abdominal organs.

The present invention may further be applied to such a device that calculates not only an index relating to the body fat but also any values, including a body water content or a muscle amount in the body, so far as the values can be calculated by using the bioelectrical impedance.

Although in the above-described embodiments of the present invention, the bioelectrical impedance and the body weight have been used respectively as the reference values with respect to one user upon making a determination, if the device has been designed such that the measured data is stored therein for each time slot based on the measurement time obtained in the clock circuit, then the comparison with the reference values set for the corresponding time slot of measurement may become possible and thus the determination of the measured subject may be achieved with the circadian rhythm taken into account. Alternatively, if the compensation for the circadian rhythm is applied to the arithmetic formula of the approach degree described above by way of adding a compensation term corresponding to the measurement time, then it is no more necessary to store the data corresponding to each time slot and accordingly the memory region would not be increased.

Although in the above embodiments of the present invention, the device has been designed such that the measured values are used to update the reference values every time when the measurement is performed, however, alternatively, a plurality of measured values for last several measurements may be stored to take an average of those values for updating the reference values.

EFFECT OF THE INVENTION

According to the living body measuring device of the present invention as defined in claim 1, since the current measured subject is determined automatically by comparing the currently measured bioelectrical impedance value with the previously stored bioelectrical impedance value, the subject of measurement is no more required to remember his/her own memory number once his/her personal information has been set, which makes the device more user-friendly.

According to the living body measuring device of the present invention as defined in claim 2, since the current measured subject is determined automatically by comparing the currently measured bioelectrical impedance value and body weight value with those values having measured and stored previously, the determination of the measured subject may be more accurate and the device may become more user friendly to the measured subject.

According to the living body measuring device of the present invention as defined in claim 3, since the device further comprises the clock circuit and stores a measurement day and time as well, an elapsed day count from the day on which the storage means has stored the data to the current day of measurement may be apparent and the new data may be favorably used as a parameter for determination, thereby enabling a more accurate determination of the measured subject.

According to the living body measuring device of the present invention as defined in claim 4, since the data can be stored for each time slot of measurement, it can help control the affection from the circadian rhythm to the body weight and/or bioelectrical impedance, thereby enabling the more accurate determination of the measured subject.

According to the living body measuring device of the present invention as defined in claim 5, since the switch is designed such that the measurement may be started when the subject of measurement puts his/her body on the device, and all of the serial procedures from the measurement through the calculation to the result display may be executed automatically, thus the device may become more user friendly to the measured subject.

According to the living body measuring device of the present invention as defined in claim 6, since the body information used for the calculation is indicated in addition to the result indication, the user can ensure that the determination of the measured subject has been done in an appropriate manner.

According to the living body measuring device of the present invention as defined in claim 7, since an adequate data can be used to make a recalculation even in the case of the erroneous determination of the measured subject, the device may become more user friendly.

According to the living body measuring device of the present invention as defined in claim 8, since the most recently measured values have been stored and are used for the determination of the measured subject in the subsequent measurement, the device may respond to any change in the body of the measured subject and provide the more accurate determination of the measured subject.

What is claimed is:

1. A living body measuring device having a function for determining a measured subject, comprising an input unit, a bioelectrical impedance measuring unit, a storage unit and an arithmetic unit,
   wherein
   said input unit enters information relating to a body of a subject;
   said bioelectrical impedance measuring unit measures a bioelectrical impedance of said subject;
   said storage unit stores data for a plurality of subjects, said data representing the body-related information entered from said input unit and the measured bioelectrical impedance values; and
   said arithmetic unit compares the measured current bioelectrical impedance value with the bioelectrical impedance values for the plurality of subjects stored in said storage unit to automatically determine, in consideration of an elapsed day count from a last measurement day stored in said storage unit to a current measurement day, a body-related information which is to be used for calculation from among the body-related information for the plurality of subjects, and calculates an index relating to the body of the subject based on the determined body-related information and the measured current bioelectrical impedance value.

2. A living body measuring device having a function for determining a measured subject, comprising an input unit, a body weight measuring unit, a bioelectrical impedance measuring unit, a storage unit and an arithmetic unit,
   wherein
   said input unit enters information relating to a body of a subject;
   said body weight measuring unit measures a body weight of said subject;
   said bioelectrical impedance measuring unit measures a bioelectrical impedance of said subject;
   said storage unit stores data for a plurality of subjects, said data representing the body-related information entered from said input unit and measured body weight values and bioelectrical impedance values; and
   said arithmetic unit compares the measured current body weight value and bioelectrical impedance value with the body weight values and bioelectrical impedance values for the plurality of subjects stored in said storage unit to automatically determine, in consideration of an elapsed day count from a last measurement day stored in said storage unit to a current measurement day, a body-related information which is to be used for calculation from among the body-related information for the plurality of subjects and calculates an index relating to the body of the subject based on the determined body-related information and the measured current body weight value and bioelectrical impedance value.

3. A living body measuring device having a function for determining a measured subject in accordance with claim 2, said device further comprising a switch,
   wherein
   said switch is activated to measure a body weight and a bioelectrical impedance upon a subject putting his/her body on said device.

4. A living body measuring device having a function for determining a measured subject in accordance with claim 2, said device further comprising a display unit,
   wherein
   said display unit indicates an index relating to a body of a subject, said index representing a result from the calculation by said arithmetic unit, and
   said display unit also indicates the body information stored in said storage unit and used in the calculation as well as the result indication.

5. A living body measuring device having a function for determining a measured subject in accordance with claim 4, in which
   said arithmetic unit recalculates the index relating to the body based on a selected information if the information to be used in the calculation is changed during the indication of the index relating to the body.

6. A living body measuring device having a function for determining a measured subject in accordance with claim 2, in which
   a bioelectrical impedance value and a body weight value for a subject stored in said storage unit are updated at each time when the measurements are made.

7. A living body measuring device having a function for determining a measured subject in accordance with claim 2, in which
   said arithmetic unit makes a determination of a subject in favor of a result obtained from a comparison of the body weights between the comparison of body weight values and the comparison of bioelectrical impedance values.

8. A living body measuring device having a function for determining a measured subject, comprising an input unit, a bioelectrical impedance measuring unit, a storage unit and an arithmetic unit,
   wherein
   said input unit enters information relating to a body of a subject;
   said bioelectrical impedance measuring unit measures a bioelectrical impedance of said subject;
   said storage unit stores data for a plurality of subjects, said data representing the body-related information entered from said input unit and the measured bioelectrical impedance values, and in said storage unit the measured bioelectrical impedance values for each of the plurality of subjects are stored on a measurement time slot; and
   said arithmetic unit compares the stored measured values in the same time slot as the current time with the current measured value to automatically determine the body-related information which is to be used for calculation from among the body-related information for the plurality of subjects, and calculates an index relating to the body of the subject based on the determined body-related information and the measured current bioelectrical impedance value.

9. A living body measuring device having a function for determining a measured subject, comprising an input unit, a body weight measuring unit, a bioelectrical impedance measuring unit, a storage unit and an arithmetic unit,
wherein
said input unit enters information relating to a body of a subject;
said body weight measuring unit measures a body weight of said subject;
said bioelectrical impedance measuring unit measures a bioelectrical impedance of said subject;
said storage unit stores data for a plurality of subjects, said data representing the body-related information entered from said input unit and measured body weight values and bioelectrical impedance values, and in said storage unit the measured bioelectrical impedance values and the measured body weight for each of the plurality of subjects are stored on a measurement time slot; and
said arithmetic unit compares the stored measured values in the same time slot as the current time with the current measured value to automatically determine the body-related information which is to be used for calculation from among the body-related information for the plurality of subjects, and calculates an index relating to the body of the subject based on the determined body-related information and the measured current body weight value and bioelectrical impedance value.

10. A living body measuring device having a function for determining a measured subject, comprising an input unit, a bioelectrical impedance measuring unit, an electrode, a storage unit and an arithmetic unit,
wherein
said input unit enters information relating to a body of a subject;
said bioelectrical impedance measuring unit measures a bioelectrical impedance of said subject;
said electrode is used for measurement of a sole length of a subject and also the measurement of the bioelectrical impedance value at said bioelectrical impedance measuring unit, said electrode comprising a plurality of sub-electrodes;
said storage unit stores data for a plurality of subjects, said data representing the body-related information entered from said input unit, the measured bioelectrical impedance values and the sole lengths; and
said arithmetic unit compares the measured current bioelectrical impedance value and sole length with the bioelectrical impedance values and sole lengths for the plurality of subjects stored in said storage unit to automatically determine the body-related information which is to be used for calculation from among the body-related information for the plurality of subjects, and calculates an index relating to the body of the subject based on the determined body-related information and the measured current bioelectrical impedance value.

11. A living body measuring device having a function for determining a measured subject, comprising an input unit, a body weight measuring unit, a bioelectrical impedance measuring unit, an electrode, a storage unit and an arithmetic unit,
wherein
said input unit enters information relating to a body of a subject;
said body weight measuring unit measures a body weight of said subject;
said bioelectrical impedance measuring unit measures a bioelectrical impedance of said subject;
said electrode is used for measurement of a sole length of a subject and also the measurement of the bioelectrical impedance value at said bioelectrical impedance measuring unit, said electrode comprising a plurality of sub-electrodes;
said storage unit stores data for a plurality of subjects, said data representing the body-related information entered from said input unit, the measured body weight values, the bioelectrical impedance values, and the sole lengths; and
said arithmetic unit compares the measured current body weight value, bioelectrical impedance value and sole length with the body weight values, bioelectrical impedance values and sole lengths for the plurality of subjects stored in said storage unit to automatically determine the body-related information which is to be used for calculation from among the body-related information for the plurality of subjects, and calculates an index relating to the body of the subject based on the determined body-related information and the measured current body weight value and bioelectrical impedance value.

* * * * *